May 24, 1949. VINCENZO SODANO KNOWN AS JIMMY SODANO ROSE PLANT Filed April 22, 1947 Plant Pat. 840
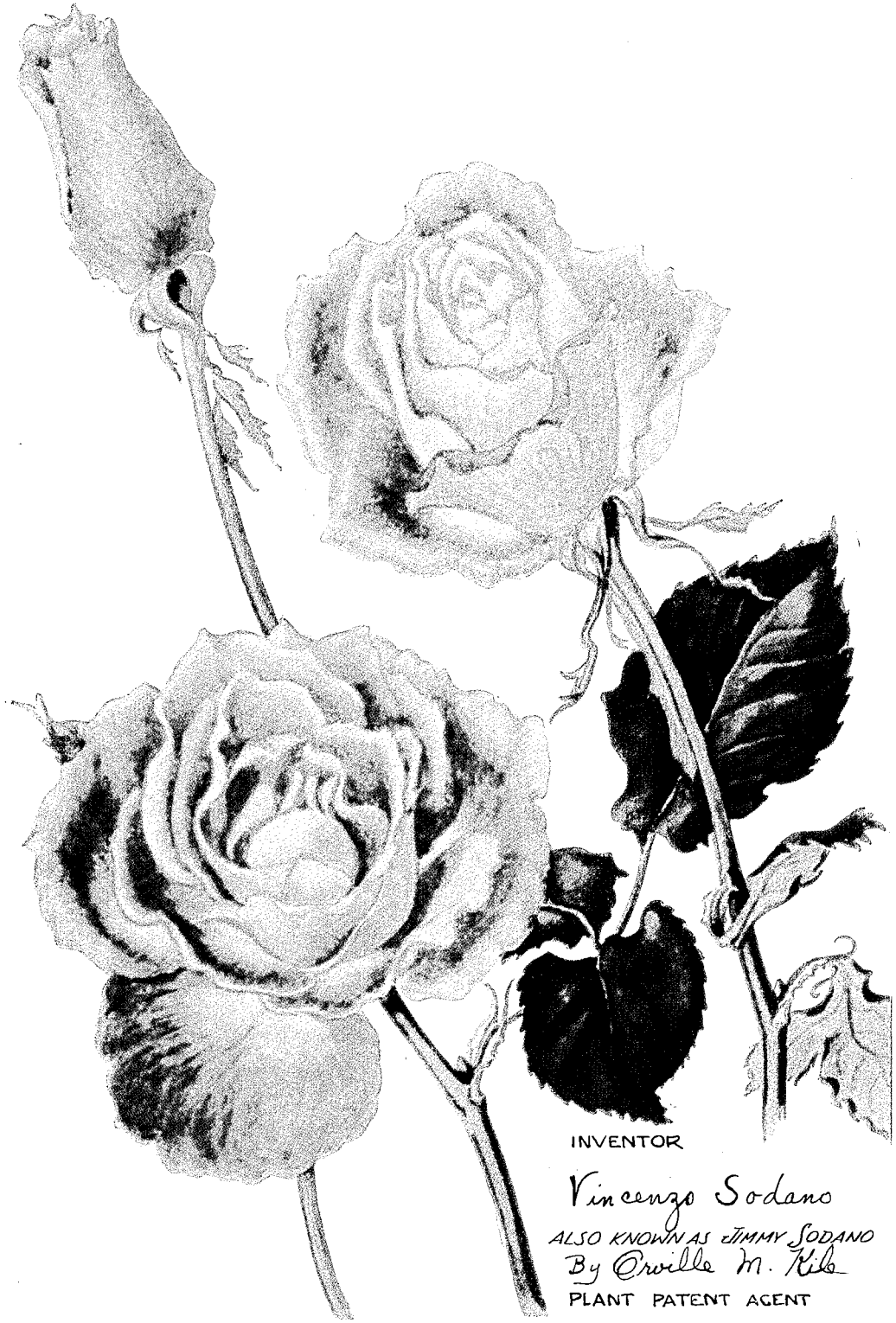

Patented May 24, 1949

Plant Pat. 840

UNITED STATES PATENT OFFICE

840

ROSE PLANT

Vincenzo Sodano, known as Jimmy Sodano,
Madison, N. J.

Application April 22, 1947, Serial No. 743,110

1 Claim. (Cl. 47—61)

My present discovery relates to an improved variety of hybrid tea rose plant of the type usually grown in greenhouses. It originated as a sport of Better Times (Plant Patent 23) and has some of the characteristics of its parent. However it differs from the parent variety in a number of important points, particularly in the larger and heavier-textured petals of the buds and flowers, the more pointed shape of the bud and flower, the deeper and more velvety color of the flower, the darker and more substantial foliage, and the more vigorous growth.

The variety has been asexually reproduced and the novel features have proved to be permanent.

The accompanying illustrations show a bud, a half-opened flower and a fully opened flower, together with portions of their stems and foliage. In the original paintings they are shown in approximately their true size and colors, and as near the velvety brilliance as is possible with the medium used.

Following is a detailed description of my new variety. Color plate numbers refer to Ridgway's Color Standards and Nomenclature, and other reference to color indicates the usual dictionary meaning of the term.

*The plant*

Growth: Very vigorous, upright bush. Free-growing, requiring much less attention than its parent. Attains height of 8 to 10 feet.

Disease resistance: Very healthy. Resistant to diseases common to roses.

Blooming habit: Continuous bloomer, producing many very large blooms. Recurrent every six weeks.

Foliage:

*Quantity.*—Abundant.

*Leaves.*—Compound, usually with 3 to 5 leaflets but with the first below the flower a single leaflet.

*Size.*—Large, with terminal leaflet measuring about 2 inches wide and 3 inches long.

*Shape.*—Ovate, with very sharp acuminate tip. Deeply and sharply serrated.

*Texture.*—Thick and leathery.

*Color.*—Dark green, approximately Empire Green (Plate XXXII). Under side tinged with red or bronze.

*New leaves.*—Approximately Brick Red (Plate XIII).

*Rachis.*—Red tinged. Smooth below and grooved above. Short, with leaflets and stipules meeting in many instances. Moderately heavy.

*Stipules.*—Long, narrow, clinging for about two-thirds their length. Points very slender.

Stems: Stiff, strong, very heavy and approximately Jade Green (Plate XXXI). Lower portion has a few large, downward-pointing thorns.

Peduncle: Lighter and brighter than stems, approximately Lettuce Green (Plate V). Smooth, strong and straight. From 4 to 6 inches in length.

Sepals: Foliaceous appendages extend beyond bud before it breaks. At least one sepal is very leaflike. Reflex early.

*The bloom*

Bud:

*Form.*—Long and pointed.

*Size.*—Typical bud measures 2 to 2½ inches in length just before beginning to unfold. This is approximately ½ inch longer than the bud of the parent.

*Opening.*—Opens slowly and evenly. Petals reflex only slightly.

*Color.*—Between Rose Color and Tyrian Rose (Plate XII) just before opening.

*Aspect.*—Silky.

Flower:

*Borne.*—Singly.

*Petalage.*—Usually 25 to 30 petals.

*Size.*—Although the petalage is not great, the flower is very large, frequently measuring 5½ to 6 inches in diameter.

*Form.*—Very high-centered and loosely furled. Centers remain high and stamens covered. Petals reflex only slightly and outer petals usually continue at right angles to the peduncle. The over-all effect of the form is somewhat similar to that of a semi-double peony.

*Color.*—The color is very difficult to describe and is not found in Ridgway's Color Standards and Nomenclature. The general color effect of a newly-opened rose is a little darker than Tyrian Rose (Plate XII), with a much greater degree of brilliance and "life." The color of the under surface of the petals at this time lies between Rose Color and Tyrian Rose (Plate XII). The color does not fade but rather grows deeper after the flower opens. On about the fourth day after opening, the color lies somewhere between Rhodamine Purple and Aster Purple (Plate XII), with the outer edges approximately the latter color. The base of the petals and their under surface is a color between Tyrian Pink and Rhodamine Purple (Plate XII).

*Aspect.*—Petals are silky on the under surface but very velvety on the upper surface, particularly toward the edges which are also darker in color. Even when the flower is old, this rich velvety aspect is retained.

Petals:

*Size.*—Outer petals are exceptionally large, measuring approximately 2¼ by 2¼ inches. The inner petals are much smaller but still large enough to form a high center which is retained.

*Texture.*—Substantial.

*Shape.*—Outer petals are modified obovate while the inner petals are from obovate to spatulate. Edges mostly entire.

*Fragrance.*—Particularly pronounced and pleasing, as well as unusually lasting.

Keeping qualities: Excellent. Flowers kept in excellent condition at room temperatures for five days after having been shipped by mail. When kept at cooler temperatures, they kept well for a week or more.

Reproductive organs:

*Pistils.*—Moderate quantity, tightly bunched. Styles short and tinged with red. Stigmas yellow.

*Stamens.*—Many, surrounding pistils. Filaments longer than pistils; purplish red. Anthers yellow and relatively large.

*Comparison with Better Times*

My new variety differs from its parent, the Better Times, principally in the following respects:

*Plant.*—The foliage and stems of my new variety are thicker and darker. The plant is much more vigorous. It grows much freer and requires less attention.

*Bud.*—The bud of my new variety is ½ inch longer and much more pointed.

*Flower.*—The shape of the flower of my new variety is pointed and the high-centered form is retained, whereas the parent flower is globular and opens flat. The flower of my variety is much darker in color and very much more velvety in aspect; also this color does not fade but deepens in tone. Petals are larger and of heavier texture, although there are fewer of them.

Having thus disclosed my discovery, I claim:

The new and distinct variety of hybrid tea rose plant, substantially as herein shown and described, characterized particularly by the large dark green foliage devoid of thorns; its free and vigorous growth; the large size of its flowers and petals; its lasting fragrance; the retained high-centered form of the flowers as well as the unruffled and only slightly reflexed edge of the petals; and the velvety brilliance of its newly-opened flowers of dark Tyrian Rose which deepens as the flower ages.

VINCENZO SODANO.

REFERENCES CITED

The following references are of record in the file of this patent:

UNITED STATES PATENTS

| Number | Name | Date |
|---|---|---|
| Pl. Pt. 295 | Ringdahl | Oct. 18, 1938 |
| Pl. Pt. 688 | Sodano | May 14, 1946 |
| Pl. Pt. 743 | Krowka | July 8, 1947 |